US010195267B2

(12) United States Patent
Knolle et al.

(10) Patent No.: US 10,195,267 B2
(45) Date of Patent: Feb. 5, 2019

(54) VACCINATION STRATEGY

(71) Applicants: RHEINISCHE FRIEDRICH-WILHELMS UNIVERSITÄT BONN, Bonn (DE); TECHNISCHE UNIVERSITÄT MÜNCHEN, München (DE); HELMHOLTZ ZENTRUM MÜNCHEN DEUTSHES FORSCHUNGSZENTRUM FÜR GESUNDHEIT UND UMWELT (GMBH), Neuherberg (DE)

(72) Inventors: Percy Knolle, München (DE); Li-Rung Huang, Bonn (DE); Mathias Heikenwälder, München (DE); Ulrike Protzer, München (DE)

(73) Assignees: KLINIKUM RECHTS DER ISAR DER TECHNISCHEN UNIVERSITÄT MÜNCHEN, München (DE); TECH UNIVERSITÄT MÜNCHEN, München (DE); HELMHOLTZ ZENTRUM MÜNCHEN—DEUTSCHES FORSCHUNGSZENTRUM FÜR GESUNDHEIT UND UMWELT, Neuherberg (DE)

( * ) Notice: Subject to any disclaimer, the term of this patent is extended or adjusted under 35 U.S.C. 154(b) by 0 days.

(21) Appl. No.: 14/769,987

(22) PCT Filed: Feb. 25, 2014

(86) PCT No.: PCT/EP2014/053603
§ 371 (c)(1),
(2) Date: Aug. 24, 2015

(87) PCT Pub. No.: WO2014/128305
PCT Pub. Date: Aug. 28, 2014

(65) Prior Publication Data
US 2016/0008460 A1  Jan. 14, 2016

(30) Foreign Application Priority Data
Feb. 25, 2013  (EP) .................................... 13156546

(51) Int. Cl.
A61K 39/00  (2006.01)
A61K 39/39  (2006.01)
A61K 39/29  (2006.01)
C12N 7/00  (2006.01)

(52) U.S. Cl.
CPC ............ A61K 39/292 (2013.01); A61K 39/39 (2013.01); C12N 7/00 (2013.01); A61K 2039/525 (2013.01); C12N 2730/10134 (2013.01); C12N 2730/10171 (2013.01)

(58) Field of Classification Search
CPC ................ A61K 2300/00; A61K 39/12; A61K 2039/55561; A61K 2039/53; A61K 39/145; A61K 39/245; A61K 38/00; A61K 2039/6075; A61K 39/205; A61K 39/215; A61K 39/275; C12N 2740/16234; C12N 2730/10134
See application file for complete search history.

(56) References Cited

PUBLICATIONS

Kwissa et al. J Exp Med. Oct. 29, 2007;204(11):2733-46. Epub Oct. 22, 2007.*
Immunity. Jul. 25, 2013; 39(1): 38-48. doi:10.1016/j.immuni.2013. 07.004.*
Smyth et al. International Immunopharmacology 15 (2013), pp. 67-72, published on line on Nov. 14, 2012.*
Liu et al. Journal of Immunology, 2010, vol. 184, pp. 3367-3376.*
Dasari et al. Journal of General Virology, 2011, vol. 92, pp. 1021-1031.*
Cooper J. Clin. Immunol. 2004, vol. 24 (6), pp. 693-701.*
Muraoka Daisuke et al, "Peptide Vaccine Induces Enhanced Tumor Growth Associated With Apoptosis Induction in CD8(+) T Cells," Journal of Immunology, Sep. 15, 2010, pp. 3768-3776, vol. 185, No. 6, Baltimore, MD.
Li Rung Huang et al, "Transfer of HBV Genomes Using Low Doses of Adenovirus Vectors Leads to Persistent Infection in Immune Competent Mice," Gastroenterology, Mar. 3, 2012, pp. 1447-1450, vol. 142, No. 7, Elsevier, Philadelphia, PA.
Melief Cornelis J M et al, "Effective Therapeutic Anticancer Vaccines Based on Precision Guiding of Cytolytic T Lymphocytes," Immunological Reviews, Oct. 1, 2002, pp. 177-182, vol. 188.
Huang Li-Rung et al, "Intrahepatic Myeloid-Cell Aggregates Enable Local Proliferation of CD8(+) T Cells and Successful Immunotherapy Against Chronic Viral Liver Infection," Nature Immunology, Jun. 2013, pp. 574-583, vol. 14, No. 6.

* cited by examiner

Primary Examiner — Bao Q Li
(74) Attorney, Agent, or Firm — Grogan, Tuccillo & Vanderleeden, LLP

(57) ABSTRACT

In a first aspect, the present invention relates to the use of a TLR 9 agonist and/or a TLR 4 agonist in a prophylactic or therapeutic vaccine. According to the present vaccination strategy, the TLR 9 agonist and/or TLR 4 agonist is adapted or designed for use as a multiplying jump agent to enhance numbers and functionality of CD8 T cells in a prime-jump vaccination strategy for jump T cell expansion. In particular, the TLR 9 agonist and/or TLR 4 agonist is used as a component to be administered after priming of the individual to be vaccinated. The vaccination strategy is particularly useful against acute and chronic infections with intracellular pathogens or for anti-tumor vaccination. In another aspect, the present invention relates to a kit of part containing a prime agent and a multiplying jump agent according to the present invention.

10 Claims, 5 Drawing Sheets

Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: artificial
<220> FEATURE:
<223> OTHER INFORMATION: synthetic nucleid acid oligonucleotide

<400> SEQUENCE: 1
tccatgacgt tcctgatgct                                                   20

<210> SEQ ID NO 2
<211> LENGTH: 20
<212> TYPE: DNA
<213> ORGANISM: artificial
<220> FEATURE:
<223> OTHER INFORMATION: synthetic nucleic acid oligonucleotide

<400> SEQUENCE: 2
tccatgagct tcctgatgct                                                   20

<210> SEQ ID NO 3
<211> LENGTH: 8
<212> TYPE: PRT
<213> ORGANISM: artificial
<220> FEATURE:
<223> OTHER INFORMATION: synthetic peptide

<400> SEQUENCE: 3

Ser Ile Ile Asn Phe Glu Lys Leu
1               5
```

VACCINATION STRATEGY

CROSS-REFERENCE TO RELATED APPLICATIONS

This application is entitled to the benefit of and incorporates by reference essential subject matter disclosed in International Application No. PCT/EP2014/053603 filed on Feb. 25, 2014, and German Patent Application No. 13156546.7 filed on Feb. 25, 2013.

In a first aspect, the present invention relates to the use of a TLR 9 agonist and/or a TLR 4 agonist in a prophylactic or therapeutic vaccine. According to the present vaccination strategy, the TLR 9 agonist and/or TLR 4 agonist is adapted or designed for use as a multiplying jump agent to enhance numbers and functionality of CD8 T cells in a prime-jump vaccination strategy for jump T cell expansion. In particular, the TLR 9 agonist and/or TLR 4 agonist is used as a component to be administered after priming of the individual to be vaccinated. The vaccination strategy is particularly useful against acute and chronic infections with intracellular pathogen and against cancers of any kind. In another aspect, the present invention relates to a kit of part containing a prime agent and a multiplying jump agent according to the present invention.

PRIOR ART

Various strategies are known for vaccination of individuals. Typically, a vaccination strategy is based on repetitive administration of the vaccine to the individual. By consecutive administration of the vaccine, the immune system should elicit an immune response against the antigen or pathogen to be vaccinated against.

Various strategies exist. For example, common strategies are based on administration of antigenic components at predetermined time points. Typically, the antigenic components are administered together with adjuvants for enhancing the immune response in the individual. Vaccination may be conducted either therapeutically or prophylactically. While prophylactic vaccination strategies aim to stimulate the individual's immune system in developing preventive adaptive immunity to a pathogen, the goal of therapeutic vaccination strategy is to combat persisting infections or diseases, like cancer, present in the individuals body.

Vaccination should allow immunisation of said individual by developing immunological memory and protective immunity against the immunogen (antigen) present in the vaccine.

Typically, the immunisation enables the development of memory B cells and memory T cells being responsible for a swift response during a second encounter with the antigenic structure or immunogen.

Various vaccine strategies are adapted to allow the development of suitable memory B cell responses as well as memory T cell responses, namely, vaccination strategies to strengthen the antibody-based immune response, i.e. the humoral immune response. These vaccination strategies have been developed to allow prophylactic vaccination.

For example, a hepatitis B vaccine is known relating to a vaccine developed for the prevention of hepatitis B virus infection. Typically, a course of two to three vaccine injections are given, the second injection at least one month after the first dose and the third injection being administered six months after the first dose. The vaccination aims to establish antibodies against hepatitis B, that is, establishing a humoral immune response effective in preventing infection by hepatitis B. Hepatitis B is an infectious inflammatory illness of the liver caused by the immune response against hepatitis B virus representing a typical example of an intracellular pathogen infecting chronically humans.

Further, vaccination strategies against intracellular pathogens or cancer cells have been described, that is, therapeutic vaccination strategies. Muraoka, d., et. al., J. Immunol, 2010, 185(6), 3768-3776 reports on peptide vaccines inducing enhanced tumor growth associated with apoptosis induction in CD8 T cells. Therein, the use of a TLR9 ligand or TLR9 agonist, CpG, is described as an adjuvant given simultaneously with the antigen resulting reduction of apoptosis in induction in effector CD8 T cells. Melief. C. J. M., et al., 2002 Immunol. Review, 177-182 review effective therapeutic anticancer vaccines based on precision guiding of cytotoxic T lymphocytes. Therein, the use of TLR9 ligands or TLR9 agonists as well as TLR4 agonists as adjuvants are described that are co-administered together with the antigen.

The liver is an organ with unique immune functions that are determined by its particular microenvironment and its organ-resident antigen-presenting cells. Because of this distinct regulation of T cell responses the liver is considered to be a lymphoid organ. Although the immune system is in principle capable of clearing infections of the liver caused by viruses, bacteria or parasites, certain infections with hepatotropic pathogens such as Hepatitis B Virus (HBV) or Hepatitis C Virus or malaria parasites can persist and establish a chronic infection, which affects hundreds of millions of people worldwide. Several molecular mechanisms limiting the function and expansion of cytotoxic CD8+T cells (CTLs) have been reported for the liver, such as ubiquitous expression of inhibitory molecules like PDLL and Galectin-9, expression of enzymes metabolizing amino acids required for T cell expansion like arginase or release of immune-regulatory cytokines like IL-10 and TGFb (Protzer, U., et al., Nat Rev Immunol 12, 201-213 (2012)). These regulatory cues limit CTL function in the liver, which may serve to protect the infected liver from overwhelming immunopathology by inducing an oscillatory CTL effector function (Isogawa, M., et al., Immunity 23, 53-63 (2005)) but may also result in functional exhaustion or clonal elimination of pathogen-specific CTLs (Das, A. et al., J Exp Med 205, 2111-2124 (2008). However, it was shown that large numbers of parasite-specific CTLs were able to eradicate infected hepatocytes indicating that the number of CTLs required to find and eliminate infected hepatocytes within the maze of liver sinusoids is critical for successful immune control of infection. Thus, the generation of large numbers of CTLs seems to be an important element for overcoming chronic infection. At present, no convincing immunotherapy for treatment of chronic viral infection of the liver or for treatment of intracellular pathogens in the liver or other pathogens of an individual as well as strategies for combating persistent tumors in an individual exists. Although adjuvant based vaccination strategies exist for generation of cellular immune responses, successful expansion of CTLs and eradication of the targets, like intracellular pathogens or tumors are not described in the art.

The generation of sufficient numbers of CTLs for defense against pathogens is regulated by the extent of antigen-presentation through appropriately matured dendritic cells in secondary lymphatic tissue. In addition, CTLs may proliferate within infected tissues after exit from lymph nodes upon MHC-I-restricted activation through the T cell receptor, but local regulatory cues in the hepatic microenvironment limit or even prevent such local expansion. During chronic inflammation the generation of tertiary lymphatic tissue was reported to increase local T cell priming and thereby augment the numbers of CTLs within chronically inflamed tissue (Neyt, K., et al., Trends in immunology 33, 297-305 (2012)). The generation of tertiary lymphatic tissue in lung increased immunity during influenza infection. No reports on the relevance of tertiary lymphatic tissue for chronic infection of the liver exist to date. Also, knowledge on the mechanisms that allow local expansion of CTLs in infected tissues, particularly the liver, is lacking.

Hence, there is still a demand for new vaccine strategies and new vaccines allowing improved vaccination against intracellular pathogens, e.g. intracellular pathogens persisting in organs and establishing a chronic infection, as well as against tumor cells, that result in massive expansion of CTLs.

SUMMARY OF THE INVENTION

The inventors found that the TLR 9 and/or TLR 4 agonist is useful in a prophylactic or therapeutic vaccine whereby said TLR 9 agonist and/or TLR 4 agonist is adapted or designed for use as a multiplying jump agent to enhance numbers and functionalities of CD8 T-cells in a prime jump vaccination strategy for jump T-cell expansion.

Further, the present invention relates to a vaccination strategy including the use of TLR 9 agonist and/or TLR 4 agonist as a multiplying jump agent to enhance numbers and functionality of CD8 T-cells in a prime-jump strategy whereby the priming agent is an antigen derived from the intracellular pathogen or the tumour cell to be vaccinated against while the TLR 9 agonist and/or TLR 4 agonist is a known agonist to be administered at least six days, preferably at least eight days after the administration of the priming agent, particularly preferably within a time limit of 10 to 20 days.

It is preferred, that the TLR9 and/or TLR4 agonists are used in prophylactic or therapeutic vaccine strategies in disease entities where CD8 T cells responses are of therapeutic value, such as chronic viral infection, like hepatitis B infection, or cancer. In a further embodiment of the present invention, a kit of part containing the prime agent and the multiplying jump agent for enhancement of numbers and functionality of CD8 T cells in a prime-jump-vaccination-strategy for jump CD8 T cell expansion whereby the multiplying jump agent is a TLR 9 agonist and/or TLR 4 agonist together with instruction for use thereof according to the present invention is provided.

DETAILED DESCRIPTION OF THE PRESENT INVENTION

Figure 1A:
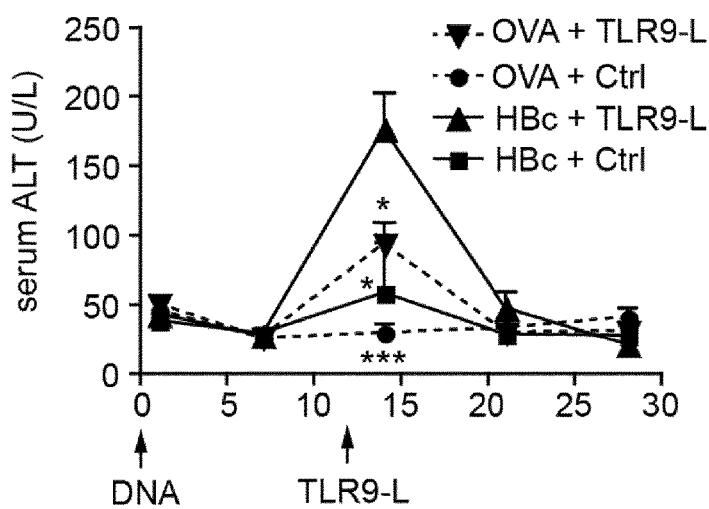
FIG. 1. Elimination of chronic HBV infection (a) Mice with chronic AdHBV-infection after $1\times10^8$ ifu AdHBV-infection. Time course of serum ALT following HBc-DNA vaccination (d0) and TLR9-L or CTRL treatment (d12). OVA-DNA vaccination as control. (n=5 per group). (b-f) At d15 after vaccination, (b) immunohistochemistry for CD11 b and CD8 in the liver as described in (a) at d15 after vaccination; (c) increase of $HBc_{93-100}$-specific CTLs in spleen and liver detected by dextramer-staining. (n=3 per group), ND, not detectable; (d) IFN$\gamma$-producing $HBc_{93-100}$-specific CTLs isolated from livers of mice after HBc-peptide-specific restimulation ex vivo; (e) total numbers of IFN$\gamma$-producing $HBc_{93-100}$-specific CTLs after peptide-specific restimulation ex vivo per gram liver (n=3, per group); (f) PD-1 expression levels on $HBc_{93-100}$-specific CTLs directly ex vivo. (g) Serum HBeAg levels from mice as described in (a). (h) Immunohistochemical detection and (i) quantification of HBcore-Ag-positive hepatocytes at d42 after vaccination. HPF, high power field (magnification, 100.times.). *P<0.05, P<0.01, *P<0.001 (paired Student's t-test). Data are representative of three experiments (a, c, d, e, f, g) or two experiments (b, h, i) (a, c, e, i; error bars, s.d.).

In a first aspect, the present invention relates to a TLR 9 agonist and/or TLR 4 agonist for use in a prophylactic or therapeutic vaccine whereby said TLR 9 agonist and/or TLR 4 agonist is adapted or designed for use as a multiplying jump agent enhancing the number and functionality of CD8 T cells in a prime jump vaccination strategy for jump T cell expansion.

The term "jump agent" as used herein refers to an agent which is able to enhance the number of CD8 T cells also identified herein as cytotoxic effector T cells, as well the functionality of said CD8 T cells. Enhancement of the number of CD8 T cells identifies that the number of CD8 T cells after administration is increased at least 5 fold in peripheral organs such as the liver. In particular, the jump agent is not an adjuvant for simultaneous administration together with the antigen.

The term "functionality of CD8 T cells" as used herein refers to an increased cytokine expression as well as to an increased cytotoxicity of the CD8 T cells.

The term "TLR9 agonist" or TLR4 agonist" is used herein interchangeably with the terms "TLR9 ligand" and TLR4 ligand".

The term "prime-jump-vaccination strategy" as used herein refers to a vaccination strategy for expansion of CD8 T cells. Said strategy differs from other vaccination strategies including the prime boost vaccination strategy. While the prime-boost strategy aims to establish a memory B cell and T cell response in the future, other strategies which are also sometimes referred to as prime-boost-strategies aim to enhance or prolong the current immune response by administering "boosting" agents shortly after the priming. Prime-boost vaccination strategies aim to augment immunity by increasing the number of effector CD8 T cells stemming and matured from central memory T cells that reside in lymphatic tissue. In contrast, the prime-jump-vaccination strategy according to the present invention aims in directly expanding effector CD8 T cells, i.e. increasing the number of effector CD8 T cells, from the pool of organ-resident effector memory T cells and cytotoxic effector cells present in the subject.

The prime step is typically a step of antigen administration either in form of a single compound (immunogen) or in form of a mixture, e.g. in form of isolated RNA or DNA coding for the desired immunogen, together with an adjuvant, while the jump agent as defined herein expands previously activated CD8 T cells in an antigen-independent fashion.

The term "jump T cell expansion" as used herein refers to the expansion of effector CD8 T cells. Said CD8 T cells are increased in number and display an increased functionality as defined herein.

As used herein, the terms "comprising", "comprises" and "comprised of" are synonymous with "including", "includes" or "containing", "contains" and are inclusive and open ended and do not exclude additional, non-recited members, elements or method steps. It will be appreciated that the terms "comprising", "comprises", and "comprised of" as well as "including", "includes", or "containing", "contains" as used herein comprise the terms "consisting of", "consist" and "consist of".

All references cited in the present specification are hereby incorporated by reference in their entirety. In particular, the teachings of all references herein specifically referred to are incorporated by reference.

Unless otherwise identified, all terms used in disclosing the invention, including technical and scientific terms, have the meaning as commonly understood by one of the ordinary skilled in the art to which this invention belongs. By means of further guidance, term definitions are included to better appreciate the teaching of the present invention.

As used herein, the similar forms "a", "an" and "the" include both singular and plural references unless the context clearly dictates otherwise.

It is preferred, that the TLR 9 agonist and/or TLR 4 agonist according to the present invention is a TLR 9 agonist and/or TLR 4 agonist adapted or designed for use as a multiplying jump agent to enhance numbers and functionality of CD8 T cells to be administered at least six days, preferably, at least eight days after the administration of the priming agent. For example, the multiplying jump agent according to the present invention including the TLR 9 agonist and/or TLR 4 agonist is adapted or designed to be administered at least 10 days after the administration of the priming agent, e.g. 12 days.

According to the present invention, the multiplying jump agent may be a composition of a TLR 9 agonist and/or TLR 4 agonist, that is, the TLR 9 agonist or the TLR 4 agonist may be administered alone or in combination.

The TLR 9 agonist and/or TLR 4 agonist are adapted or designed for use as a multiplying jump agent to be administered at least 10 days, preferably within a time range of 10 to 20 days after administration of the priming agent. As used herein, the term "adapted or designed" refers to embodiments wherein the compounds are provided in a form to be used as defined. For example, the compounds are provided in a state allowing administration to a subject in an amount sufficient to elicit the desired effect.

The skilled person is well aware of suitable TLR 9 agonists and/or TLR 4 agonists. For example, the TLR 9 agonist is a CpG oligonucleotide, in particular, a CpG oligodeoxynucleotide. The TLR 4 agonist may be a TLR 4 agonist known in the art, for example, a monophosphoryl lipid A compound.

The present inventors recognized that TLR 9 and/or TLR 4 agonist allows to expand activated CTLs in the liver whereby a priming step was conducted in advance.

In another embodiment, the present invention relates to a TLR 9 agonist and/or TLR 4 agonist for use in a prophylactic or therapeutic vaccine against infection with an intracellular pathogen or for use in an antitumor vaccine. In particular, the compounds are for use in a therapeutic vaccine.

It is particularly preferred that the intracellular pathogen is a viral pathogen, an intracellular bacterial pathogen or an intracellular parasite. For example, the viral pathogens are any hepatitis viruses including hepatitis B or C, persisting in the liver. Examples for parasites include Shistosoma spp. or Plasmodia spp.

That is, the usefulness of the TLR 9 and/or TLR 4 agonist according to the present invention is in particular true for infections in the liver. Moreover, the TLR 9 agonist and/or TLR 4 agonist according to the present invention is useful in a prophylactic or therapeutic vaccine against a chronic or acute infection, in particular, a chronic or acute viral infection, like chronic infections of the liver, e.g. by hepatitis B or hepatitis C.

It has been recognized that the TLR 9 agonist and/or TLR 4 agonist as used according to the present invention allows to enhance locally the numbers and functionality of CD8 T cells, in particular, are useful for local enhancement of numbers and functionality of CD8 T cells in the liver. As demonstrated herein, applying the present prime-jump-vaccination-strategy according to the present invention allows to expand the CTLs locally, e.g. in the liver. For example, in a tertiary structure, in the following also called iMATEs (interhepatic myeloid cell aggregates that enable T cell expansion) enabling CTL proliferation in the liver. That is, surprisingly, a substantial proliferation of effector CD8 T cells can be observed in the newly formed iMATE structures whereby the iMATE driven proliferation does not require antigen and does not require previous contact with lymphoid tissues. Since the iMATE structure occurs temporarily only, the desired CTL expansion in these structures requires the delayed administration of the jump agent after the initial priming of CD8.sup.+ T cells. In a further aspect, the present invention relates to the use of TLR 9 agonist and/or TLR 4 agonist and their therapeutic vaccine against cancer, in particular, hepatocellular carcinoma or cholangiocarcinoma but also other hepatic malignancies. In particular, metastatic types of carcinoma may be treated.

In an embodiment of the present invention, the multiplying jump agent for enhancement of numbers and functionality of CD8 T cells contain as active ingredient the TLR 9 agonist and/or TLR 4 agonist only. In an alternative embodiment, other active ingredients may be present. Said active ingredients include antigen-dependent and/or antigen-independent activating components.

The prime agent useful according to the present invention in the prime-jump-vaccination strategy identified herein is typically an antigenic compound derived from an intracellular pathogen or tumour cells. For example, in case of vaccination against hepatitis B, in particular, therapeutic vaccination against hepatitis B, the antigenic compound present in the prime agent for use in the prime-jump-vaccination-strategy for secondary CD8 T cell expansion, in particular, for local jump CD8 T cell expansion in an individual, is derived from the hepatitis B virus to be vaccinated against.

It is preferred that the TLR 9 agonist and/or TLR 4 agonist used according to the present invention is adapted or designed to be administered intravenously, to a vascularised area or an area with induced hyperperfusion that allows rapid delivery to the liver, like the earlobe. Of course, administration may be effected by suitable routes, however, it is preferred to administer the jump agent in a way that a local enhancement of CTLs is achieved. The TLR 9 agonist and/or TLR 4 agonist may be prepared in a suitable form for the desired way of administration. Typically, the composition includes other components, like diluents, expients or carrier. Typically, pharmaceutically or therapeutically acceptable carrier is a carrier medium, which does not defer the effectiveness of the biological activity of the active ingredient and being not toxic to the host or patient. The skilled person is well aware of pharmaceutically acceptable components useful according to the present invention. As identified, the TLR 9 agonist and/or TLR 4 agonist is adapted for intravenous administrations, e.g. to human beings. Typically, compositions for intravenous administration are solutions in sterile isotonic aqueous buffer. Where necessary, other compositions may also include an agent being a local anaesthetic, such as lidocaine to ease pain at the side of the injection. The compounds according to the present invention, namely TLR 9 agonists and/or TLR 4 agonists, are in a therapeutical or pharmaceutically effective amount present in the composition administered to the individual. In this connection, the term "therapeutically or pharmaceutically effective amount" as used herein refers to the amount of compositions to induce the desired biological result. That is, to enhance numbers and functionalities of CD8 T cells, in particular, local enhancement of numbers and functionality of CD8 T cells in the prime-jump-vaccination-strategy.

The skilled person is well aware of the fact that the therapeutically or pharmaceutically effective amount may vary depending on various parameters including age, body weight, general health, sex, diet, time of administration etc. which will be ascertainable by those skilled in the art.

Moreover, the present invention relates to a kit of part containing a prime agent and a multiplying jump agent for enhancement of numbers and functionality of CD8 T cells in a prime-jump-vaccination-strategy for jump CD8 T cell expansion whereby said multiplying jump agent is a TLR 9 agonist and/or TLR 4 agonist as described herein. Said kit of pat contains in addition instructions for use thereof according to a method as defined herein.

These and other embodiments are disclosed and encompassed by the description and examples of the present invention. The present invention relates to the detailed further by way of examples without limiting the same thereto.

Examples

Material and Methods

Mice

C57BL/6j and C57BL/6N mice, actin-EGFP mice, CD11c.DOG mice, CCR2-YFP-DTR mice (Hohl, T. M. et al, Cell host & microbe 2009, 6: 470-481) OX40.sup.−/− mice, TLR9.sup.−/−, TNFR1/2.sup.−/−, CCR2.sup.−/−, Rag2.sup.−/− and CD80/86.sup.−/− mice were maintained under SPF conditions in the central animal facility of the University. All animal experiments were performed in accordance with German legislation governing animal studies and the Principles of Laboratory Animal Care guidelines (National Institutes of Health publication 85-23, 1996 revision).

Reagents

Antibodies used for flow cytometry were purchased from e-Bioscience if not otherwise indicated: PerCp-Cy5.5-conjugated anti-CD8a (53-6.7), APC-conjugated anti-CD45.1 (A20), APC-conjugated anti-CD90.1 (HIS51), PerCp-Cy5.5 or PE-conjugated anti-CD11b (M1/70), PE-conjugated anti-NKp46 (29A1.4), Alexa Huor 647 or Alexa-405-conjugated anti-mouse CD146 (ME9F1), APC-eHuor 780-conjugated anti-MHC II (I-A/I-E) (M5/114.15.2), eHuor 450 or PE-Cy5-conjugated anti-F4/80 (BM8), APC or Alexa Huor 488-conjugated anti-CD11c (N418), PE-conjugated anti-CD107b (Mac-3, M3/84), PE-conjugated anti-CD19 (eBio1D3), PE-conjugated anti-PD-1 (J43), FITC-conjugated anti-CD69 (H1.2F3), PE-conjugated anti-OX40 (OX-86) and PE-conjugated anti-CD28 (37.51); FITC-conjugated anti-Ly6C (1G7.G10) was from Miltenyi Biotec, PE-conjugated anti-Ly6G (1A8) and APC-conjugated anti-CD64 (X54-5/7.1) were from Biolegend.

TLR9L 1668 (CpG ODN 1668: 5'-S-TCCATGACGTTC-CTGATGCT-3' SEQ. ID. No. 1) or control non-TLR9 ligand (non-CpG ODN 1720: 5'-STCCATGAGCTTCCTGAT-GCT-3', SEQ. ID. No. 2) were from TIP MOLBIOL); Cy5-labeled TLR9-L was from Sigma-Aldrich, TLR3-L (Poly(I:C) VACCIGRADE™) TLR4-L (MPLA VACCIGRADE™) and TLR7-L (IMIQUIMOD VACCIGRADE™) were from InvivoGen.

Cell-type specific depletion was performed one day before and one day after TLR9-L injection: phagocytic cells with clodronate liposomes, Ly6G.sup.+ neutrophils with anti-Ly6G (100.mu.g/mouse, clone 1A8), NK cells with anti-NK1.1 (300.mu.g/mouse, clone PK136), diphtheria toxin (30 ng per gram body weight) i.p. in CCR2-YFP-DTR or CD11c.DOG transgenic mice. FTY720 was used at 1 mg/kg bodyweight to block lymphocyte egress from lymphatic tissues.

Bromodeoxyuridine (0.8 mg/mL) was applied in the drinking water and incorporation was detected by BrdU flow kit according to the manufacturer's instructions (BD Biosciences). Generation of Activated CD8.sup.+ T Cells (CTLs)

Splenic CD8.sup.+ T cells were isolated by immunomagnetic separation using CD8 microbeads (Miltenyi Biotec). Purified CD8.sup.+ T cells were stimulated for 3 days with anti-CD3/CD28 labeled T-activator Dynabeads® (Invitrogen) together with 5 ng/ml IL-12 p70 in RPMI 1640 medium (Invitrogen) supplemented with 8% FCS, 50.mu.M ME, glutamine and antibiotics. After magnetic removal of Dynabeads living were separated from dead cells with LSM 1077 lymphocyte separation medium (PAA Laboratories). For in vivo tracking of CTLs not bearing congenic markers, cells were labeled with 2.mu.M carboxyfluorescein diacetate succinimidyl ester (CFSE, Invitrogen). If not otherwise stated, 2.times.10.sup.6 activated CTLs were adoptively transferred into recipient mice.

How Cytometry and FACSorting

All stainings for flow cytometry were performed in the presence of 10.mu.g/mL of Fc block (2.4G2) in fluorescence-activated cell sorting buffer [FACS buffer, phosphate-buffered saline/1% bovine serum albumin/0.02% NaAz]. Acquisition and data analysis was conducted on a Cantoll or LSR Fortessa (BD Biosciences) and HowJo sofware (Tree Star Inc.). To exclude dead cells, Hoechst 33258 (10.mu.g/mL) (Sigma-Aldrich) or LIVE/DEAD Fixable Dead Cell Stain Kit (Invitrogen) were used.

For FACSorting of liver sinusoidal endothelial cells, Kupffer cells, $CD11b^+Ly6C^{hi}MHC\ II^-$, $CD11b^+Ly6C^{hi}MHC\text{-}II^+$ and $CD11b^+Ly6C^{dim}MHC\text{-}II^+$ from the livers of mice at d3 after of TLR9-L application, nonparenchymal cells from these mice were labeled with AlexaFluor 488-conjugated anti-CD146 (ME9-F1), PE-conjugated anti-I-A$^b$ (AF6-120.1), PerCp-Cy5.5-conjugated anti-CD11b (M1/70), APC-conjugated anti-Ly6C (HK1.4) and APC-eFluor780®-conjugated anti-F4/80 (BM8) in the presence of 10.mu.g/mL of Fc block (2.4G2) in FACS buffer for 20 minutes on ice and washed twice. Cells were filtered through a 100-.mu.m mesh after adding Hoechst 33258 to exclude dead cells and subjected to cell sorting using a FACSDiva sorter (BD Biosciences Pharmingen). Mice were depleted of NK cells and neutrophils by injection of anti-NK1.1 and anti-Ly6G antibodies at d-1 day before harvesting the livers. For FACSorting of splenic $CD44^{lo}CD127^+KLRG1^-CD8\alpha^+$ (naive) or $CD44^{hi}CD127^+KLRG1^-CD8\alpha^+$ (memory) T cells, total $CD45.1^+$ splenic $CD8^+$ T cells were enriched using $CD8\alpha^+$ T cell isolation kit II, mouse (Miltenyi Biotec) and stained with FITC-conjugated anti-KLRG1 (2F1), PE-conjugated anti-CD44 (IM7), PerCp-Cy5.5-conjugated anti-CD8.alpha. (53-6.7) and APC-conjugated anti-CD127 (A7R34) in the condition described previously followed by FACSorting.

Models for Acute Adenoviral and LCMV Infection

Recombinant adenovirus (AdLGO) expressing a fusion protein of click-beetle luciferase (Promega), enhanced green fluorescent protein (EGFP) (Promega) and H-2-K$^b$-restricted epitope OVA$_{257\text{-}264}$ (SIINFEKL, SEQ. ID No. 3) or AdLG expressing only luciferase and EGFP was used to infect C57BL/6J mice at $1\times10^6$ ifu/mouse. Two days after infection, $1\times10^4$ or $1\times10^5$ anti-CD3/28/IL-12-activated $CD90.1^+$OT I $CD8^+$ T cells were transferred together with 20.mu.g of TLR9-L or CTRL. In vivo bioluminescence to measure luciferase activity as an indicator for specific CTL activity in the liver was performed as reported (Stabenow et al. Hepatology 2010; 51:1430-37; Wohlleber et al. Cell Reports 2012; 2:478-87).

Chronic lymphocytic choriomeningitis virus (LCMV) infection was induced by infecting newborn mice with $1\times10^6$ ifu of WE LCMV. Ten weeks after infection, mice were used for experiments. LCMV-specific CTLs were obtained from spleens of mice at d7 after acute LCMV-infection ($2\times10^4$ ifu).

Chronic AdHBV Infection and Immunization

C57BL/6J mice were infected with $1\times10^8$ ifu AdHBV intravenously leading to chronic AdHBV infection, as reported previously (Huang et al. Gastroenterology 2012; 142:1447-50). DNA immunization was performed as described (Huang et al. Gastroenterology 2012; 142:1447-50). After immunization, HBeAg and serum ALT (alanine aminotransferase) activity measured using GPT strips on a REFLOVET™ Plus reader (Roche) were checked at indicated time points. Livers were collected for immunohistochemical analysis. Analysis of CTL number and function ex vivo was done as described previously (Huang et al. Gastroenterology 2012; 142:1447-50).

TCM were isolated from spleen and lymph-nodes and TEM from livers of $CD45.1^+$ mice 8 weeks after LCMV infection and FACSorted according to CD62L expression levels on the population of $CD8^+CD44^{hi}$ T cells. $10^6$ CTLs were adoptively into $CD45.2^+$ mice also injected with TLR9-L.

Liver Histology and Electron Microcopy

Preparation of liver sections for immunohistochemical staining was described previously (Wolf et al. Cancer Cell 2012; 22, 91-105). Detection of CD11 b, MHC II, CCR2, GFP, Ki-67, CD90.1, NKp46, CD19, Ly6C/Ly6G, OX40L, and BrdU was done by using M1/70 (BMA Biomedicals AG), M5/114.15.2 (Novus Biologicals), MC-21 anti-GFP polyclonal Ab (Fitzgerald Industries), SP6 (Lab Vision), anti-NKp46 polyclonal Ab (R&D), 1D3, HIS51, Gr-1 (all BD Pharmingen), 7D6 (Abcam) and B44 (BD), respectively. Preparation of liver tissues for electron microcopy was done as described previously (Wohlleber et al. Cell Reports 2012; 2:478-87)

Results iMATEs Facilitate CTL-Mediated Clearance of Viral Infection in the Liver Efficient CTL expansion within iMATEs led the inventors to investigate whether this could improve CTL immunity against viral infection in the liver. We transferred in vitro activated OVA-specific $CD90.1^+$OT-1 CTLs into TLR9-L-treated mice that had been infected with a recombinant adenovirus expressing OVA and luciferase as a fusion protein (AdLOG) (Stabenow, D. et al., Hepatology, 51, 1430-1437 (2010)). The decline of in vivo bioluminescence in this model quantifies antiviral CTL activity in vivo against infected hepatocytes more sensitively than measurement of serum ALT. We transferred low numbers of OT-I CTLs ($10^4$) into mice that were infected with $10^6$ infectious units (ifu) AdLOG. This did not significantly reduce in vivo bioluminescence, nor did TLR9-L application alone. The low numbers of transferred CTLs and infected hepatocytes resemble the situation during acute infection. CTL-transfer together with TLR9-L application, however, efficiently controlled hepatic viral luciferase expression within 4 d.

This raised the question whether iMATEs could enhance antigen-specific CTL responses. We transferred low numbers ($1\times10^5$) of activated OT-I CTLs into mice that were infected with low dose ($1\times10^6$ ifu/mouse) AdLGO or AdLG. There was an increase in numbers of hepatic OT-I CTLs in AdLG infected mice that also received TLR9-L. However, in TLR9-L-injected mice infected with AdLGO we observed a further 7 fold expansion of OT-I CTLs; also in the absence of TLR9-L challenge there was an increase in OT-I CTLs compared to mice infected with AdLG. Interestingly, we observed iMATE formation upon AdLG infection in the absence of TLR9-L injection but did not detect any OT-I CTLs within iMATEs. iMATEs also formed in AdLGO-infected mice but these iMATEs now contained many OT-I CTLs. These data suggest that viral infection of the liver caused iMATE formation and that iMATEs amplified antigen-specific CTL responses locally in the liver. Upon TLR9-L injection, the formation of iMATEs was further improved and more OT-I CTLs were observed in AdLGO-infected compared to AdLG or mock-treated mice, compatible with the more rapid control of viral infection. Interestingly, single OT-I CTLs were found in the vicinity of iMATEs implying that they executed their effector function against virus-infected hepatocytes after having left the iMATEs.

To further confirm the physiological relevance of iMATEs during viral infection we investigated iMATE formation during infection with a replication-competent virus, LCMV. During acute infection with LCMV we observed development of iMATEs formed by CD11b.sup.+ MHC-II.sup.+ cells with a peak at d9 post infection coinciding with the peak of T cell expansion. CD8.sup.+ T cells were abundant in iMATEs during acute LCMV infection suggesting that iMATEs contributed to CTL defense against LCMV infection. Prevention of iMATE formation in CCR2-CFP-DTR mice led to reduced generation of LCMV gp33-specific CTLs and failure to control LCMV replication, which may point to a role for iMATEs in LCMV-specific CTL immunity although we cannot exclude that systemic depletion of CCR2.sup.+ cells additionally influences immunity against LCMV. These results led us to investigate whether iMATEs are absent in mice suffering from chronic LCMV infection. Indeed, no iMATEs were observed in livers of chronic LCMV-infected mice but they can be induced by TLR9-L injection, suggesting that iMATEs may be employed to overcome T cell exhaustion observed during chronic viral infection. To test this hypothesis, we adoptively transferred in vivo primed splenic LCMV-gp33-specific CTLs (10.sup.6 LCMV-specific CTLs/mouse)-isolated from mice at d7 after acute LCMV infection—together with TLR9-L or CTRL at d0, d7 and d10 into mice with chronic LCMV-infection. Transfer of LCMV-specific CTLs or TLR9-L application alone did not lead to significant increases in numbers of LCMV-specific CTLs at d14 after the first transfer. After transfer of LCMV-specific CTLs together with TLR9-L injection we observed a significant increase in the numbers of LCMV gp33-specific CTLs in the liver. More importantly, LCMV titers in serum and liver dropped to background levels after combinatorial treatment with LCVM-specific CTL transfer together with TLR9-L injection. These results indicate a role for iMATEs during acute viral infection to facilitate TLR9-L-induced CTL expansion to increase anti-viral immunity and suggest that reconstitution of iMATEs that lack in chronic infection, improves CTL-mediated control of viral infection.

Successful Immunotherapy of Chronic AdHBV Infection

Figure 1B:
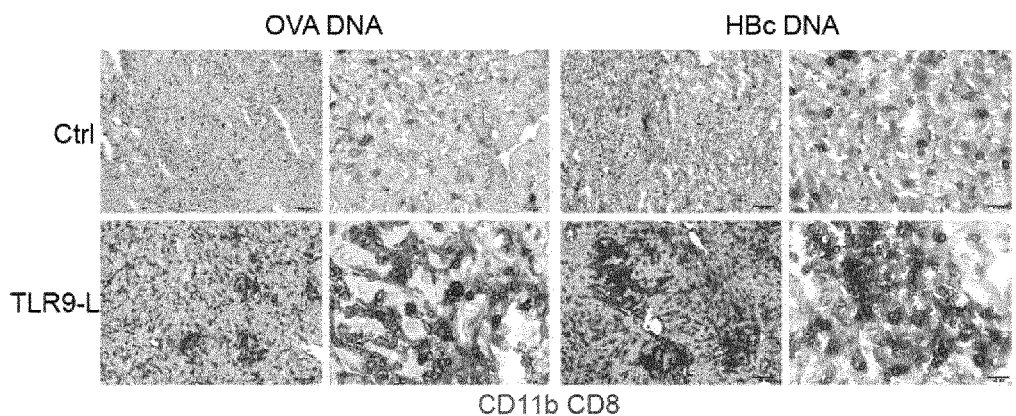

To further explore whether hepatic CTL expansion also improved defense against a chronic infection with a pathogen relevant to humans, we employed a recently established model for chronic Hepatitis B Virus (HBV) infection in immuno-competent mice through low-dose infection with AdHBV (Huang, L. R., see above). In this model, therapeutic DNA-vaccination leads to a weak increase in circulating HBV-specific CTLs but fails to control chronic_AdHBV infection. Mice with chronic AdHBV infection were subjected to DNA-vaccination with plasmids coding for the HBV core (HBc) antigen or OVA and received TLR9-L treatment 12 d later. This led to a transient rise in serum ALT indicating a low degree of liver damage, which was most pronounced in HBc-vaccinated mice receiving TLR9L treatment (FIG. 1a). We did not detect iMATEs in mice with chronic AdHBV-infection irrespective of whether they were vaccinated with DNA coding for OVA or HBcore (FIG. 1b), which indicates that increasing numbers of virus-specific CTLs were not sufficient to cause iMATE formation during chronic infection. However, TLR9-L injection induced iMATE formation in mice with chronic AdHBV-infection (FIG. 1b) raising the question whether this may facilitate expansion of HBV-specific CTLs and clearance of chronic AdHBV infection.

Figure 1C:
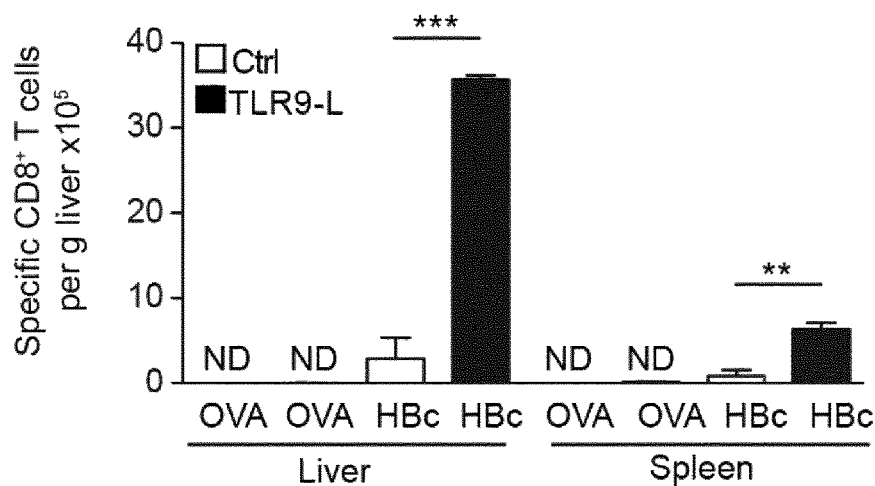
Figure 1D:
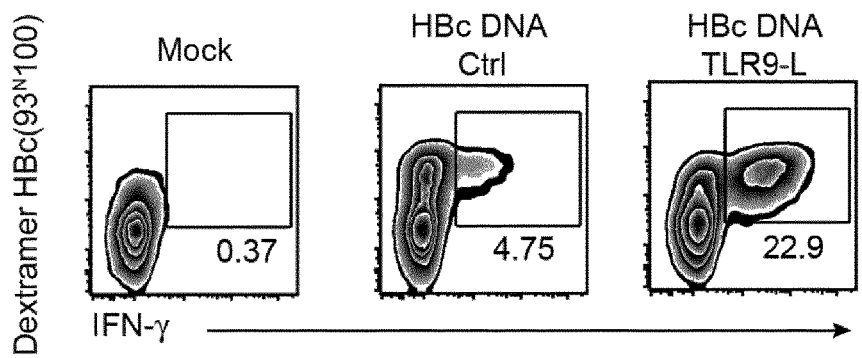
Figure 1E:
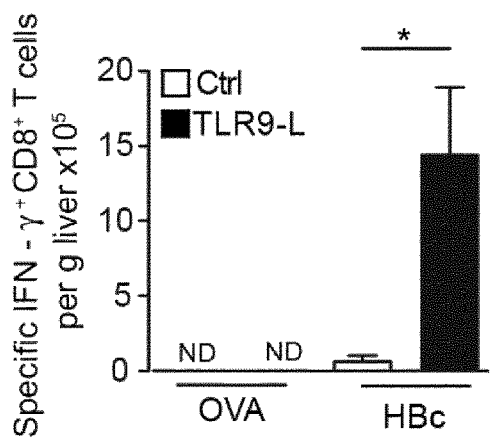
Figure 1F:
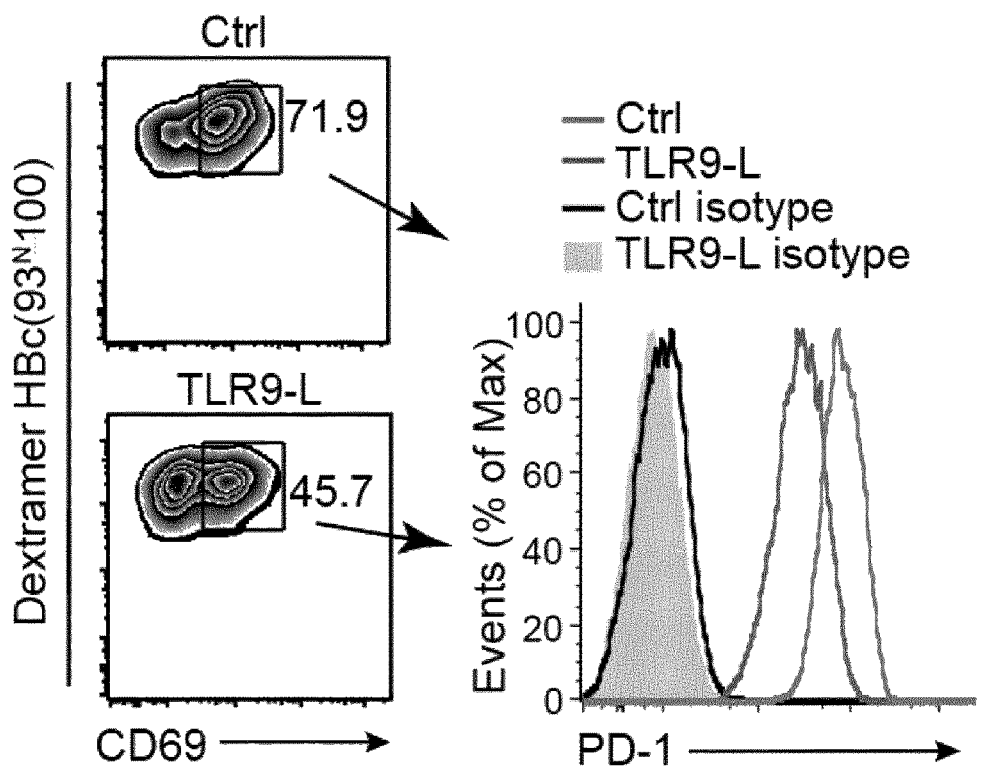
Figure 1G:
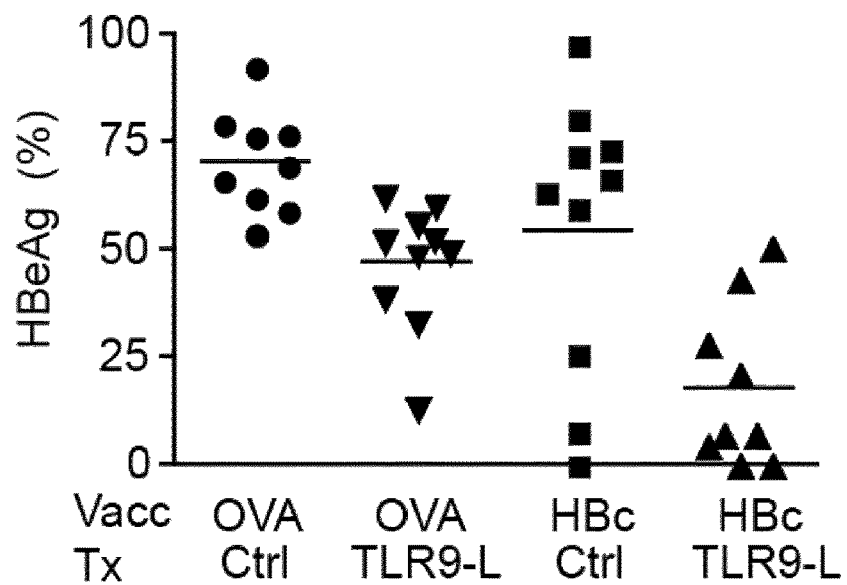
Figure 1H:
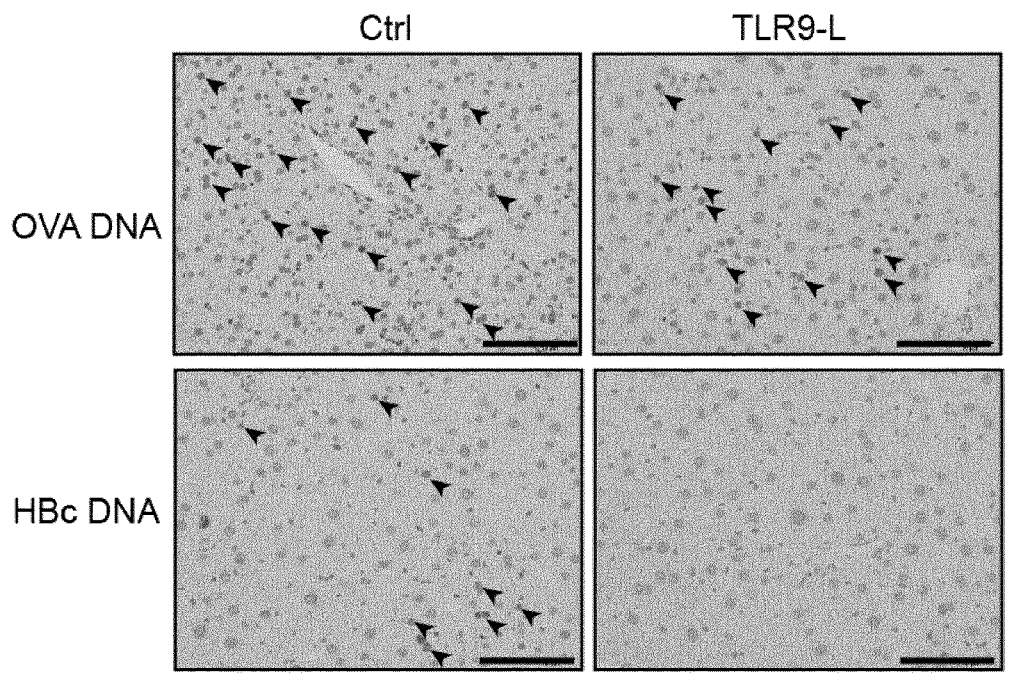
Figure 1I:
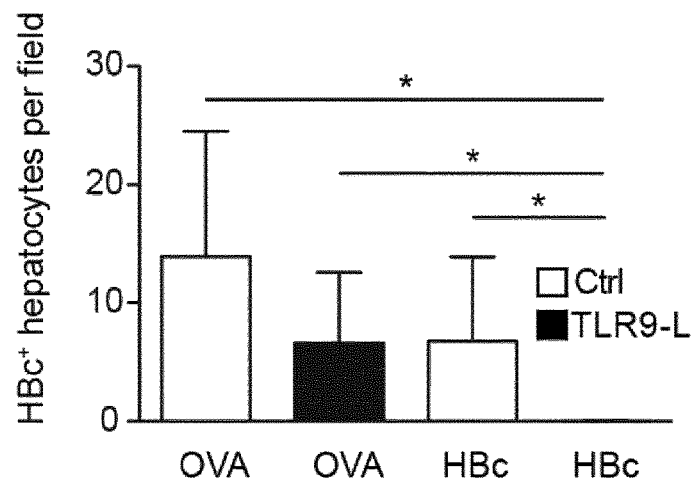

TLR9-L injection at d12 after HBcore-DNA vaccination led to pronounced expansion of HBc-specific CTLs in livers of mice with chronic AdHBV infection (FIG. 1c). These HBcore-specific CTLs were functional and expressed IFN.gamma. upon antigen-specific restimulation ex vivo, whereas in the absence of TLR9L application no IFN.gamma.-expressing HBc-specific CTLs were detected (FIGS. 1d and e). Furthermore, we observed lower expression levels of the co-inhibitory receptor PD1 on recently activated CD69.sup.+ HBcore-specific CTLs (FIG. 1f) suggesting that this DNA-vaccination in combination with iMATE induction overcame immune regulatory mechanisms that impair clearance of viral infection from the liver.sup.4. HBc-DNA vaccination in combination with TLR9-L application led to significant downregulation of serum HBeAg levels after 28 d and elimination of HBV-infected hepatocytes at d42 (FIG. 1g-i). These findings indicate that hepatic expansion of HBc-specific CTLs eradicates HBV-infected hepatocytes during chronic infection and thereby leads to viral clearance.

Figure 2:
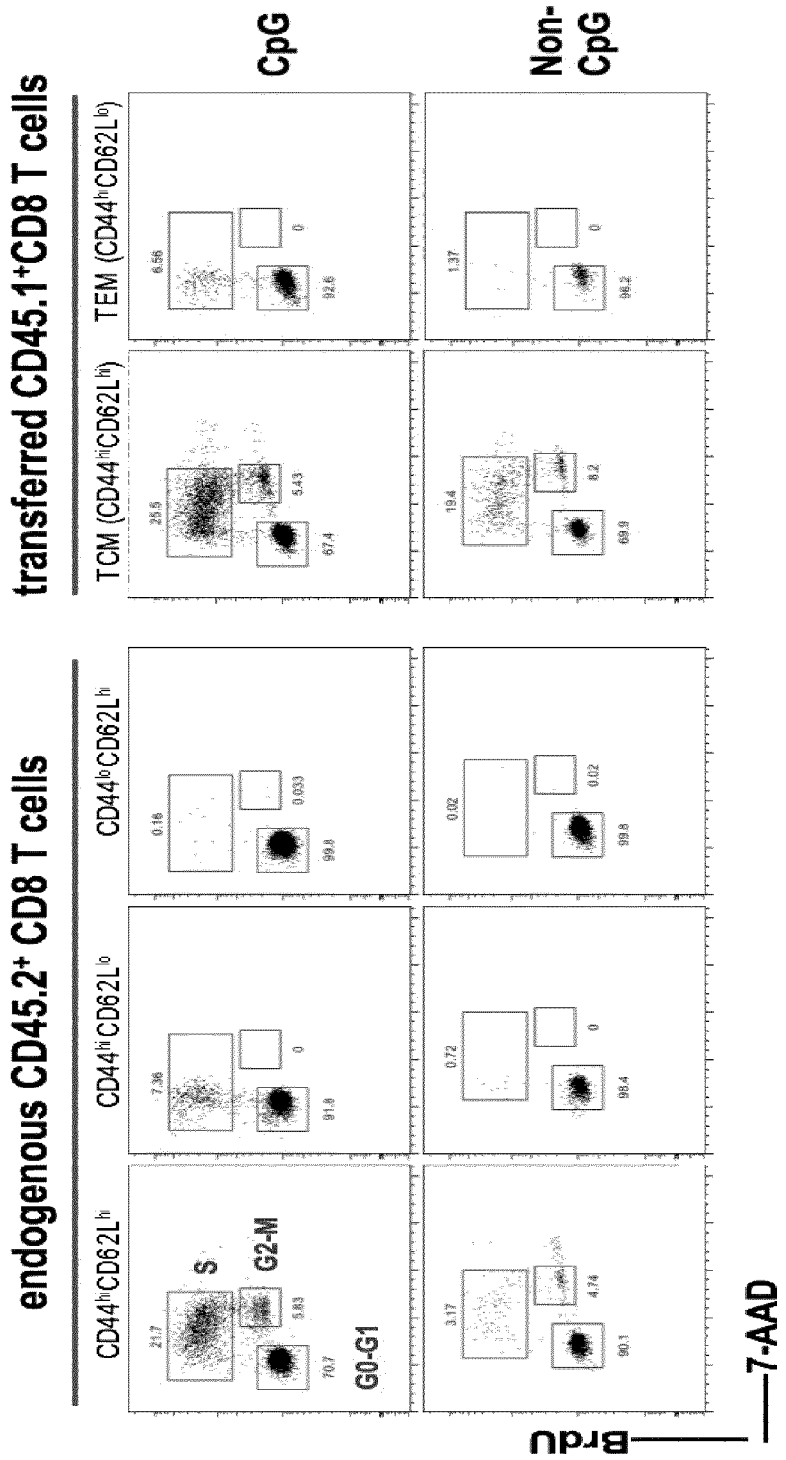
FIG. 2: Proliferation of particular CD8 T cell populations in the liver after prime-jump vaccination strategy. Central memory $CD8^+$ T cells (TCM) ($CD44^{hi}$ $CD62L^{hi}$) T cells or effector memory $CD8^+$ T cells (TEM) ($CD44^{hi}$ $CD62L^{low}$) were FACSorted from $CD45.1^+$ animals 8 weeks after LCMV infection and adoptively transferred into $CD45.2^+$ recipient mice. All cells are negative for KLRG1, that is, being not short-lived effector cells. Induction of iMATEs was achieved by intravenous injection of TLR9-ligand. After 3 days, animals were injected ip with BrdU and after a chase of 15 minutes, animals were sacrificed and livers analysed for the presence and proliferation of CD8+T cells. Shown is the flow cytometric analysis of proliferation based on BrdU-incorporation and 7-AAD staining in CD8+T cells isolated from the liver. Adoptively transferred TCM showed strong proliferation as detected by the large percentage of cells being in S and G2-M phase. Importantly, also TEM showed marked proliferation in the presence of iMATEs, i.e. after CpG application. Also endogenous $CD45.2^+CD8^+$ T cells proliferated within iMATEs; clearly, only antigen-experienced $CD44^{hi}$ $CD8^+$ T cells but not naive $CD4410$ $CD8^+$ T cells proliferated. Moreover, both $CD62L^{hi}$ as well as $CD62L^{low}$ $CD8^+$ T cells proliferated after TLR9L-application. These results demonstrate that administration of TLR9 ligand leads to proliferation of TEM and TCM in the liver.

To characterize whether iMATEs also serve as expansion hubs for effector CTLs, we adoptively transferred central memory T cells (TCM) and effector memory T cells (TEM). Upon induction of iMATEs we observed proliferation TCM as shown by incorporation of BrdU, which was expected given the known capacity of TCM to give rise to effector T cell progeny (FIG. 2). Importantly, TEM also showed proliferation in the liver after induction of iMATEs demonstrating for the first time that effector T cells can undergo proliferation in a peripheral tissue.

Discussion

We discovered that CTL activation by simultaneous stimulation through the TCR, CD28 and IL-12 in vitro, together with systemic application of TLR9-L led to a 50-fold expansion of CTLs locally in the liver. Myeloid cell aggregates, herewith termed iMATEs, which formed in the liver upon TLR9-signaling, facilitate massive CTL expansion, which contributes to anti-viral immunity and overcomes chronic viral infection in mice.

iMATEs are distinct from lymphoid structures arising during chronic inflammation. Tertiary lymphoid tissue forming in peripheral organs upon chronic inflammatory signaling is functionally and structurally similar to secondary lymphatic tissue, i.e. having germinal centers and T cell zones and antigen-sampling for DC-mediated CTL expansion (Neyt, Trends in Immunology 2012; 33:297-305). Granulomas generated during chronic inflammation or infection with intracellular bacteria are characterized by dense accumulation of macrophages surrounded by a ring of epithelial cells (Ramakrishnan, Nat. Rev. Immunol. 2012; 12:352-66). Tertiary lymphatic tissue and granuloma are considered long-lived yet dynamic structures that are constantly shaped by environmental factors. In contrast, iMATEs arise rapidly after a single injection of TLR9-L, are composed of monocyte-derived CD11b.sup.+ cells that are not demarcated from surrounding liver tissue and dissolve within 6 to 8 days. Also the mechanisms driving iMATE formation are distinct from those operating in lymphatic tissue development. While LT.beta.R signaling is crucial for secondary lymphatic tissue formation, IL-17 generates tertiary lymphatic tissue in a lymphotoxin-independent fashion in lung or the central nervous system (Peters et al. Immunity 2011; 35:986-96). We demonstrate that iMATE formation did not depend on LT.beta.R signaling but rather requires TNF receptor signaling. Monocyte-derived inflammatory dendritic cells that form iMATEs independent of crosstalk with lymphocytes produce TNF, which suggests that TNF acts in a local feed-forward loop to drive the efficient generation of iMATEs.

iMATE induction through TLR9-signaling overcomes local hepatic regulatory cues by creating a separate anatomic cocoon-like structure within the liver, where CTLs are likely to be sheltered from local inhibitory signals. Intravital imaging revealed that T cells remained stationary or migrated within the boundaries of iMATEs. As there is no fibrous capsule or ring of fibrocytes around iMATEs locally expressed chemotactic signals presumably keep CTLs within iMATEs but the factors determining CTL retention or exit from iMATEs remain to be defined. Three-dimensional reconstruction revealed that CTLs are embedded within iMATEs in a matrix of monocyte-derived inflammatory dendritic cells that likely function as nursing cells to foster CTL expansion by providing co-stimulatory signals through the OX40L-OX40 axis. CTL expansion in iMATEs occurs in the absence of MHCI-restricted antigen recognition, although we cannot exclude a role for MHCI-induced tonic TCR signaling under these circumstances that is important for keeping T cells in a state where they can respond to subsequent antigen-specific stimulation (Hochweller et al. Proc. Natl. Acad. Sci. USA 2010; 107:5931-36). However, in the presence of their cognate antigen in infected hepatocytes CTL expansion in iMATEs is improved, which indicates that inflammatory dendritic cells may cross-present antigens on MHCI to CTLs.

The generation of iMATEs during acute viral infections strongly suggests that iMATEs do not represent an artifact observed after TLR9-L challenge. iMATEs formed during acute viral infection serve as expansion hubs for antigen-specific CTLs that later on contribute to clearance of viral infection. Interestingly, no iMATEs were detected in the liver during chronic viral infection, which indicates that generation of iMATEs is correlated with efficient CTL-mediated control of viral infection and opens up the possibility to use induction of iMATEs for therapeutic vaccination.

CTL expansion in iMATEs induced by a single TLR9-L application did not trigger autoimmunity. Only continuous TLR9-L application over weeks together with large numbers of auto-reactive CTLs and hepatocellular expression of the auto-antigen caused autoimmunity (Sacher et al Eur. J. Immunol 2002; 32; 3628-37). Also chronic TLR signaling and inflammation enhances autoimmunity by increased MHCI-restricted antigen presentation and prolonged TLR3-signaling overcomes the tolerogenic hepatic microenvironment (Lang et al. J. Clin. Invest. 2006; 116:2456-63). Thus, CTL-expansion in iMATEs may improve the efficiency of therapeutic vaccines against chronic infection without causing autoimmunity.

The induction of iMATEs during chronic viral infection through application of TLR9-L caused strong expansion of virus-specific CTLs that were initially generated by genetic vaccination in vivo in the same animal. Such CTL expansion controlled chronic viral infection in hepatocytes. The combination of conventional vaccination with TLR9-L-induced CTL expansion in the liver augments the efficacy of therapeutic vaccination. Hepatic CTL expansion in iMATEs occurs independently from secondary lymphatic tissue and is therefore mechanistically distinct from T cell expansion induced by prime-boost vaccination schemes. Whereas conventional vaccination strategies aim to increase the immunogenicity of antigen presenting cells and prolong antigen presentation to naive or central memory T cells in lymphatic tissues, iMATEs expand IL12-activated CTLs but not naive and only to a lesser degree memory T cells through co-stimulatory signals and cross-presentation in the liver.

Moreover, we demonstrate that effector and effector memory CD8.sup.+ T cells proliferate within iMATEs. Since proliferation of T cells with cytotoxic effector function is very limited in peripheral organs, our discovery that TEM proliferate in livers after CpG application according to the present invention reveals a so far unrecognized mechanism to increase the number of T cells with effector function in a peripheral organ. The numbers of effector T cells present at the site of infection or within a tumor is the key denominator of protective immunity. The discovery that TCM as well as TEM employ iMATEs obtainable by a method according to the present invention for proliferation therefore provide important insight into how sufficient numbers of effector T cells can be generated in the liver.

Taken together, the present results reveal the existence of a second CTL expansion phase in the liver within a distinct anatomic compartment formed by monocyte-derived inflammatory dendritic cells. CTL expansion in iMATEs complements T cell priming and expansion within secondary lymphatic tissue resulting in massive expansion of antigen-specific CTLs in the periphery. This so far unrecognized CTL expansion phase may be employed to improve therapeutic vaccination against chronic viral infection of the liver.

In an embodiment, a method for prophylactic or therapeutic vaccination is provided wherein a TLR9 agonist and/or TLR4 agonist is administered at least 8 days after the administration of a priming agent. In other embodiments, a method for prophylactic or therapeutic vaccination is provided wherein the TLR9 agonist and/or TLR4 agonist is administered at least 10 days after the administration of a priming agent.

In another embodiment, a method for the prophylactic or therapeutic vaccination for the expansion of effector CD8 T cells includes the steps of administering a priming agent, administering a TLR9 agonist and/or a TLR4 agonist at least 6 days after the administration of the priming agent; and wherein the TLR9 agonist and/or TLR4 agonist is administered as a multiplying jump agent enhancing the number and functionality of CD8 T cells in the liver.

In another embodiment, a method for the prophylactic or therapeutic vaccination for the expansion of effector CD8 T cells includes the steps of administering an antigenic compound derived from an intracellular pathogen or cancer cells as a priming agent, administering a TLR9 agonist and/or a TLR4 agonist at least 6 days after the administration of the priming agent; and wherein the TLR9 agonist and/or TLR4 agonist is administered as a multiplying jump agent enhancing the number and functionality of CD8 T cells.

In another embodiment, a TLR 9 agonist and/or a TLR4 agonist for use in a prophylactic or therapeutic vaccine as a multiplying jump agent enhancing the number and functionality of CD8 T cells in a vaccination strategy for the expansion of effector CD8 T cells; and the TLR9 agonist and/or TLR4 agonist is administered at least 6 days, and preferably at least 8 days, after the administration of a priming agent. The agonist is for use in a vaccination strategy against infection with an intracellular pathogen, including a viral pathogen, an intracellular bacterial pathogen or an intracellular parasite, or in an anti-cancer vaccine.

In yet another embodiment, a TLR 9 agonist and/or a TLR4 agonist for use in a prophylactic or therapeutic vaccine as a multiplying jump agent enhancing locally the number and functionality of CD8 T cells in a vaccination strategy for the expansion of effector CD8 T cells in the liver; and the TLR9 agonist and/or TLR4 agonist is administered at least 6 days, and preferably at least 8 days, after the administration of a priming agent.

In another embodiment, a TLR 9 agonist and/or a TLR4 agonist for use in a prophylactic or therapeutic vaccine as a multiplying jump agent enhancing the number and functionality of CD8 T cells in a vaccination strategy for the expansion of effector CD8 T cells; and the TLR9 agonist and/or TLR4 agonist is administered intravenously or to a vascularised area at least 6 days, and preferably at least 8 days, after the administration of a priming agent.

In yet another embodiment, a TLR 9 agonist and/or a TLR4 agonist for use in a prophylactic or therapeutic vaccine as a multiplying jump agent enhancing the number and functionality of CD8 T cells in a vaccination strategy for the expansion of effector CD8 T cells; and the TLR9 agonist and/or TLR4 agonist is administered at least 6 days, and preferably at least 8 days, after the administration of a priming agent and the priming agent is an antigenic compound, derived from an intracellular pathogen or cancer cells.

4. The method for expansion of effector CD8 T cells against infection with an intracellular pathogen according to claim 3 wherein the intracellular pathogen is a viral pathogen, an intracellular bacterial pathogen or an intracellular parasite.

5. The method for expansion of effector CD8 T cells according to claim 1 wherein the vaccination is against a chronic or acute infection.

6. The method for expansion of effector CD8 T cells against a chronic or acute infection according to claim 5 when the chronic or acute infection is a chronic or acute viral infection.

The invention claimed is:

1. A method for expansion of effector CD8 T cells comprising the steps of:
   administering a priming agent,
   separately administering a TLR9 agonist at least 6 days after the administration of the priming agent; and
   wherein the TLR9 agonist is administered as a multiplying jump agent enhancing the number and functionality of CD8 T cells.

2. The method for expansion of effector CD8 T cells according to claim 1 wherein the TLR9 agonist is administered with a time range of 10 to 20 days after administration of the priming agent.

3. The method for expansion of effector CD8 T cells according claim 1 for vaccination against infection with an intracellular pathogen or cancer.

4. The method for expansion of effector CD8 T cells against infection with an intracellular pathogen according to claim 3 wherein the intracellular pathogen is a viral pathogen, an intracellular bacterial pathogen or an intracellular parasite.

7. The method for expansion of effector CD8 T cells according claim 1 wherein the TLR9 agonist is selected from CpG oligonucleotide, in particular, a CpG oligodeoxynucleotide.

8. The method for expansion of effector CD8 T cells according to claim 1 wherein administration of the TLR9 agonist is intravenously or to a vascularized area.

9. The method for expansion of effector CD8 T cells according to claim 1 wherein the TLR9 agonist is administered in a composition in which the TLR9 agonist is the only active ingredients.

10. The method for expansion of effector CD8 T cells according to claim 9 wherein the priming agent is an antigenic compound stemming from an intracellular pathogen to be vaccinated against allowing secondary CD8 T cell expansion, in particular, expansion of effector CD8 T cells.

* * * * *